United States Patent [19]

Yudelson

[11] Patent Number: 4,965,007
[45] Date of Patent: Oct. 23, 1990

[54] ENCAPSULATED SUPERPARAMAGNETIC PARTICLES

[75] Inventor: Joseph S. Yudelson, Rochester, N.Y.

[73] Assignee: Eastman Kodak Company, Rochester, N.Y.

[21] Appl. No.: 192,753

[22] Filed: May 10, 1988

[51] Int. Cl.$^5$ .......................... H01F 1/26; B01J 13/10
[52] U.S. Cl. .............................. 252/62.53; 427/213.33; 428/403; 428/407
[58] Field of Search .......................... 252/62.53, 62.54; 428/407, 403; 427/213.33, 127

[56] References Cited

U.S. PATENT DOCUMENTS

| | | | |
|---|---|---|---|
| 3,190,837 | 6/1965 | Brynko et al. | 427/213.33 |
| 3,697,437 | 10/1972 | Fogle et al. | 252/316 |
| 3,804,775 | 4/1974 | Shiozaki et al. | 427/213.33 |
| 4,019,995 | 4/1977 | Briggs et al. | 252/62.53 |
| 4,267,234 | 5/1981 | Rembaum | 428/403 |
| 4,582,622 | 4/1986 | Ikeda et al. | 252/62.53 |
| 4,604,222 | 8/1986 | Borduz et al. | 252/62.52 |
| 4,638,032 | 1/1987 | Benner | 525/54.11 |
| 4,672,040 | 6/1987 | Josephson | 436/526 |

OTHER PUBLICATIONS

Suzuki et al, *Colloids and Surfaces,* 4 (1982), pp. 163–171.
B. L. Herschbein et al., "Magnetic Separations in Chemistry and Biochemistry," 1982, *CHEMTECH,* pp. 172–179.
P. J. Robinson, "The Properties of Magnetic Supports in Relation to Immobilized Enzyme Reactors", (1973), *Biotechnology & Bioengineering,* vol. XV, pp. 603–606.
K. Mosbach et al., "Magnetic Ferrofluids for Preparation of Magnetic Polymers and their Applications in Affinity Chromatography," Nov., 1977, *Nature,* vol. 270, pp. 259–261.
Uniform Latex Particles (supplement), Seradyn Diagnostics, Inc., Apr., 1986, pp. 65–66.

*Primary Examiner*—Gary P. Straub
*Assistant Examiner*—Stephen G. Kalinchak
*Attorney, Agent, or Firm*—William J. Davis

[57] ABSTRACT

Stable, encapsulated superparamagnetic magnetite particles having a narrow particle size distribution with average particle diameters in the range of from about 50 Å to about 350 Å are prepared by forming an aqueous dispersion of magnetite particles having the above particle size characteristics in the presence of a surfactant, coacervating a mixture of gelatin and a carboxyl containing hydrophilic polymer such as gum arabic to form a thin coating of coacervate on the magnetite particles and crosslinking the coacervate coating with a gelatin hardener such as glutaraldehyde.

33 Claims, 2 Drawing Sheets

ENCAPSULATED SUPERPARAMAGNETIC PARTICLES

FIELD OF THE INVENTION

This invention relates to magnetically responsive particles and to their use in systems in which the separation of certain molecules, macromolecules and cells from the surrounding medium is necessary or desirable. More particularly, the invention relates to methods for the preparation of magnetically responsive particles comprising a magnetite core surrounded by a very thin, stable, modified gelatin coating. If desired, a wide variety of organic and/or biological molecules may be coupled to the coating. The particles (coupled or uncoupled) can be dispersed in aqueous media without rapid gravitational settling and conveniently reclaimed from the media with a magnetic field. The process provided herein yields particles that are superparamagnetic; that is, they do not become permanently magnetized after application of a magnetic field. This property permits the particles to be redispersed without magnetic aggregate formation. Hence the particles may be reused or recycled. Stability of the coating of the invention as well as of the covalent attachment of molecules thereto also facilitates the use and reuse of the encapsulated superparamagnetic particles of the invention.

The magnetically responsive particles of this invention may be coupled to biological or organic molecules with affinity for or the ability to adsorb or which interact with certain other biological or organic molecules or with cells. Particles so coupled may be used in a variety of in vitro or in vivo systems involving separation steps or the directed movement of coupled molecules to particular sites, including, but not limited to, immunological assays, other biological assays, biochemical or enzymatic reactions, affinity chromatographic purifications, nucleic acid hybridization, cell sorting, cell separation and diagnostic and therapeutic uses, including site specific drug delivery and magnetic resonance imaging.

DESCRIPTION RELATIVE TO THE PRIOR ART

Very small particles (50–350 Å region) of normally ferromagnetic materials are unable to support magnetic domains and are called superparamagnetic. This means that they are weakly magnetic in the absence of an external magnetic field, but upon the application of an external magnetic field, become magnetic and agglomerate readily. The ease with which such particles become magnetized upon application of a magnetic field is directly proportional to their degree of magnetization, measured in emu/gm (electromagnetic units per gram). Their property of becoming demagnetized upon removal of the magnetic field is inversely proportional to their coercive force, measured in Oersteds (Oe). As a practical matter, materials (particles) that have a degree of magnetization of at least about 30 emu/gm and a coercive force of less than about 30 Oe can be considered superparamagnetic. Generally, the greater the magnetization and the lower the coercive force, the more usefully or "strongly" superparamagnetic the particles become. That is, less magnetic force is required to magnetize them and they lose their magnetic properties more rapidly upon removal of the outside magnetic force. Such particles have found many uses, ranging from mechanical seals and couplings to biological separations.

A detailed review of pertinent prior art may be found in U.S. Pat. No. 4,672,040, issued June 6, 1987. As noted therein, the use of magnetic separations in biological systems as an alternative to gravitational or centrifugal separations has been reviewed by B. L. Hirschbein et al., Chemtech, March 1982: 172–179 (1982); M. Pourfarzaneh, The Ligand Quarterly, 5(1): 41–47 (1982); and P.J. Halling and P. Dunnhill, Enzyme Microb. Technol., 2: 2–10 (1980). Several advantages of using magnetically separable particles as supports for biological molecules such as enzymes, antibodies and other bioaffinity adsorbents are generally recognized. For instance, when magnetic particles are used as solid phase supports in immobilized enzyme systems [see, e.g., P. J. Robinson et al., Biotech. Bioeng., XV: 603–606 (1973)], the enzyme may be selectively recovered from media, including media containing suspended solids, allowing recycling in enzyme reactors. When used as solid supports in immunoassays or other competitive binding assays, magnetic particles permit homogeneous reaction conditions (which promote optimal binding kinetics and minimally alter analyte-adsorbent equilibrium) and facilitate separation of bound from unbound analyte, compared to centrifugation. Centrifugal separations are time consuming, require expensive and energy-consuming equipment and pose radiological, biological and physiological hazards. Magnetic separations, on the other hand, are relatively rapid and easy, requiring simple equipment. Finally, the use of non-porous adsorbent-coupled magnetic particles in affinity chromatography systems allows better mass transfer and results in less fouling than in conventional affinity chromatography systems.

Although the general concept of magnetizing molecules by coupling them to magnetic particles has been discussed and the potential advantages of using such particles for biological purposes recognized, the practical development of magnetic separations has been hindered by several critical properties of magnetic particles developed thus far.

Large magnetic particles [mean diameter in solution greater than 10 microns($\mu$)] can respond to weak magnetic fields and magnetic field gradients; however, they tend to settle rapidly, limiting their usefulness for reactions requiring homogeneous conditions. Large particles also have a more limited surface area per weight than smaller particles, so that less material can be coupled to them. Examples of large particles are those of Robinson et al., [supra] which are 50–125$\mu$ in diameter, those of Mosbach and Anderson [Nature, 270: 259–261 (1977)] which are 60–140$\mu$ in diameter and those of Guesdon et al., [J. Allergy Clin. Immunol 61(1): 23–27 (1978)] which are 50–160$\mu$ in diameter.

Ferromagnetic materials in general become permanently magnetized in response to magnetic fields. Materials termed "superparamagnetic" experience a force in a magnetic field gradient, but do not become permanently magnetized. Crystals of magnetic iron oxides may be either ferromagnetic or superparamagnetic, depending on the size of the crystals. Superparamagnetic oxides of iron generally result when the crystal is less than about 350 Å(0.035$\mu$) in diameter; larger crystals generally have a ferromagnetic character. Following initial exposure to a magnetic field, ferromagnetic particles tend to aggregate because of magnetic attraction between the permanently magnetized particles, as has been noted by Robinson et al., [supra].

As described, for example, in U.S. Pat. No. 4,604,222, superparamagnetic particles are generally prepared by ball-milling magnetic powders for long periods of time, followed by tedious sieving and purification processes. As a result, they have been extremely costly and this has limited their applications.

For use in biological separation, it is necessary to derivatize the particle so that functional groups, such as amine or carboxyl, are present at the surface for bonding to antibodies and the like. This has required the use of costly reagents, such as amine or carboxyl silanes, and the process of attachment to the magnetic particle is difficult. See U.S. Pat. Nos. 4,672,040 and 4,683,032.

The preparation of magnetite by means of hydroxide addition to a solution of ferrous/ferric salts is well known. The concept of using a dispersing agent during or after the preparation to stabilize the magnetite particles has been reported, for example in U.S. Pat. No. 4,019,995 and is the basis for a commercial product ("Lignosite") manufactured by the Georgia Pacific Corporation. However, that product consists of magnetite particles that are appended to the lignin polymer chain and are not encapsulated. The ratio of lignin to magnetite is quite large, and the product does not appear to be suitable for biological work.

Dispersible magnetic iron oxide particles reportedly having 300 Å diameters and surface amine groups were prepared by base Precipitation of ferrous chloride and ferric chloride in the presence of polyethylene imine, according to Rembaum in U.S. Pat. No. 4,267,234. Reportedly, these particles were exposed to a magnetic field three times during preparation and were described as redispersible. The magnetic particles were mixed with a glutaraldehyde suspension polymerization system to form magnetic polyglutaraldehyde microspheres with reported diameters of $0.1\mu$. Polyglutaraldehyde microspheres have aldehyde groups on the surface which can form bonds to amino-containing molecules such as proteins. However, in general, only compounds which are capable of reacting with aldehyde groups can be directly linked to the surface of polyglutaraldehyde microspheres. Moreover, magnetic polyglutaraldehyde microspheres are not sufficiently stable for certain applications.

Latex particles containing magnetite particles dispersed within the latex sphere are available in the micron (latex) range. See "Uniform Latex Particles" Seragen Diagnostics, Inc., April, 1986, supplement. These are derivatized to be used for antigen separation Large polyacrylamide-agarose particles containing finely divided magnetite are used for affinity chromatography. These particles are in the several-micron range.

U.S. Pat. No. 4,582,622 describes the preparation of a "homogenous" magnetic particulate, having a particle size of 0.8-50 $\mu$m by preparing an aqueous colloidal solution containing gelatin, a water soluble polysaccharide such as gum arabic, sodium polymetaphosphate and a ferromagnetic substance, adjusting the pH to 2.5 to 6 with an acid, and forming a water insoluble particulate by adding an aldehyde. The magnetic particulate is useful as a carrier to immobilize such biological proteins as antigens, antibodies, and enzymes for use in diagnostic assays. As shown in Example 8 (infra) however, the process of that patent, which does not use coacervation conditions as set forth herein, results in coarse aggregates having relatively large particle sizes, compared to the fine, discrete, paramagnetic coacervate coated magnetite particles of the present invention. As will be appreciated by those skilled in the art, smaller particles have larger surface areas per unit weight (or volume) than large particles, which, in turn, affords greater efficiency of use in that less small particle carrier than large particle carrier would be required to carry a given amount of immobilized biological protein. Also, the smaller size particles of the present invention are amenable to ingestion by animals for diagnostic or therapeutic use whereas the larger particles of U.S. Pat. No. 4,582,622 would be expected to be unsuitable for such use by virtue of their size. In addition, such large particles are not suitable for magnetic separation techniques such as that described in Example 1 (infra).

SUMMARY OF THE INVENTION

The present invention provides a method for preparing superparamagnetic particles of magnetite ($Fe_3O_4$) that are encapsulated by a thin layer of mo gelatin The multifunctionality of the modified gelatin makes the attachment of biologically active compounds such as antibodies very facile. In addition, the encapsulation stabilizes these very small particles.

The present invention also provides a method for preparing superparamagnetic magnetite particles that are encapsulated by a thin shell of a coacervate of gelatin and gum arabic (or another polymeric acid comprising recurring acid groups, preferably those selected from the group consisting of carboxylic acid groups and sulfonic acid groups). This procedure eliminates the need for extensive milling and grinding that have heretofore been widely used to prepare superparamagnetic particles. The encapsulation materials provide reactivity through the various functional groups present in the gelatin-gum arabic shell or coating.

DETAILED DESCRIPTION OF THE INVENTION

Figure 1:
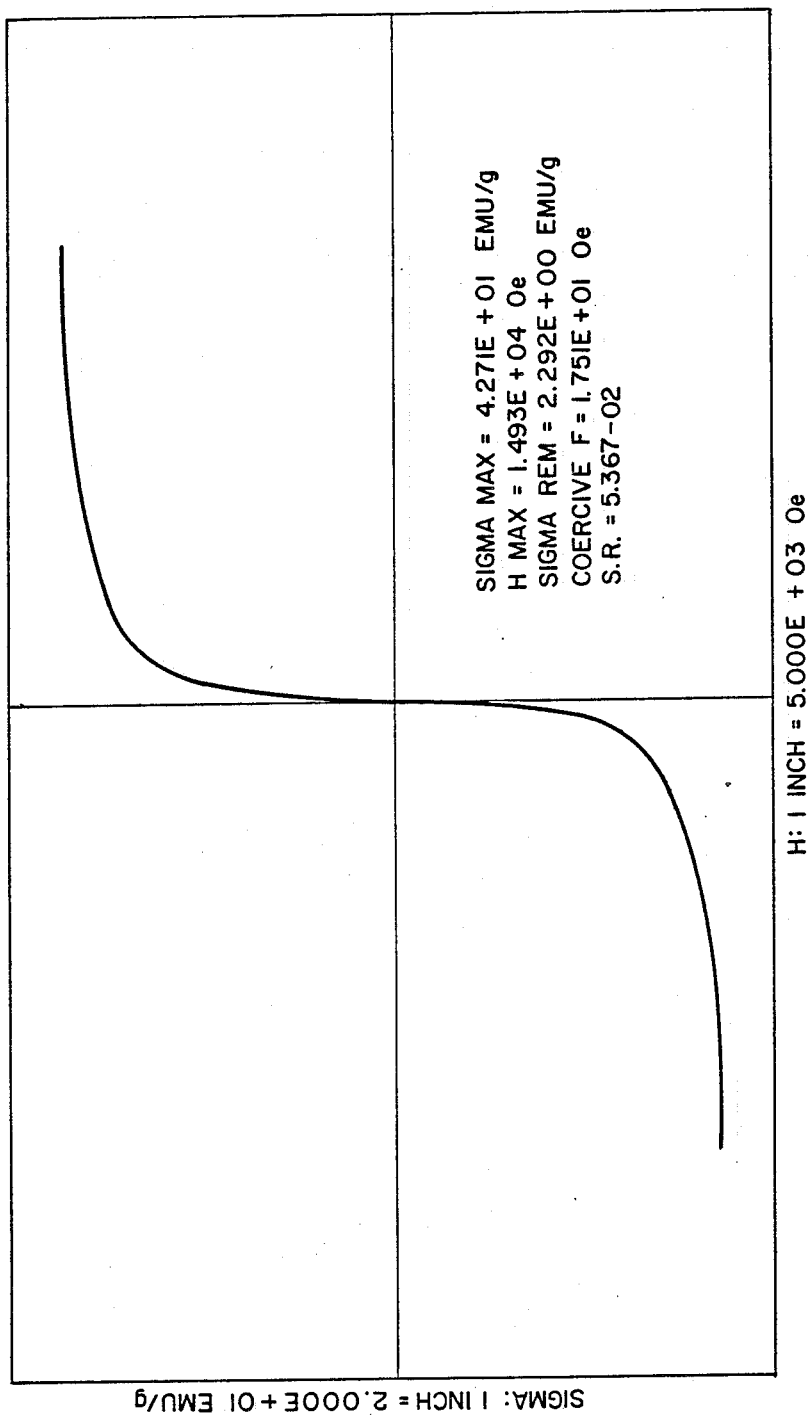
FIG. 1 is a Sigma H loop showing the magnetization curve for the encapsulated superparamagnetic magnetite particles of Example 1.
Figure 2:
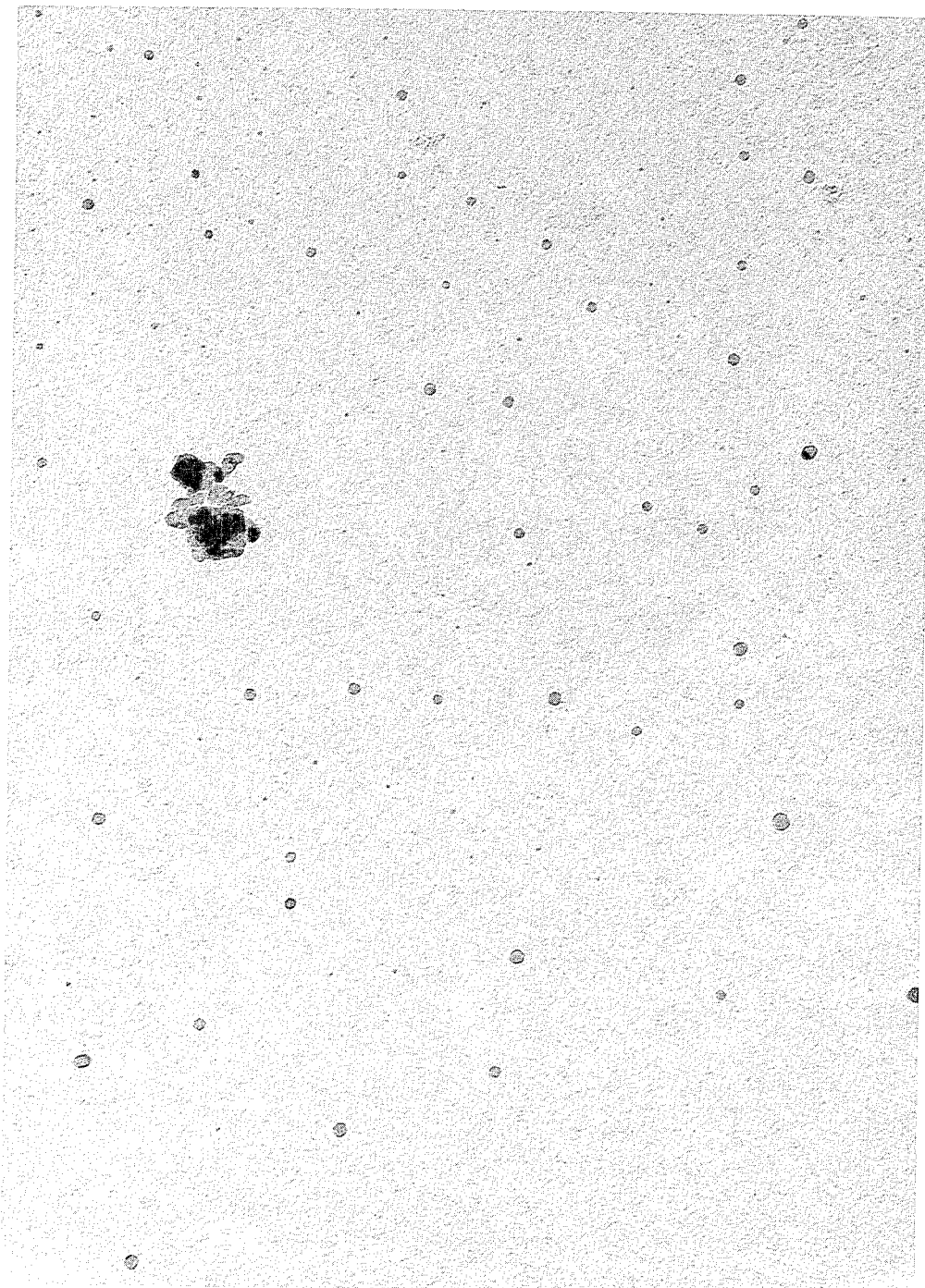
FIG. 2 is a photograph obtained by TEM (Transmission Electron Microscopy) showing the encapsulated superparamagnetic magnetite particles of Example 1, dispersed in water, at a magnification of 279,070 times.

In accordance with the present invention, superparamagnetic magnetite particles with a narrow particle size distribution in the range of from about 50 Å to about 350 Å are prepared by adding a mixture of ferric and ferrous salts to water in amounts that provide a molar ratio of ferric to ferrous ions in the range of about 1.6 to 2.4 and in concentrations in the range of 0.01 to 1 molar, preferably about 0.05 to 0.5 molar, more preferably about 0.1 molar; optionally, adding acid, e.g., sulfuric acid, to adjust the pH to less than about 1.5; preferably adding from about 0.1 to about 5% (wt/vol) of a surfactant solution; preferably purging the resulting solution of oxygen by bubbling therethrough an inert gas, preferably nitrogen, for a period of at least about 10 minutes, preferably at least about 30 minutes; adding to the (preferably purged) solution (preferably, as rapidly as possible), with stirring, concentrated NaOH (or an equivalent hydroxide, for example, ammonium, potassium, or lithium hydroxide) in an amount in excess of 8 moles of hydroxide ion per mole of Fe++ present in the solution, to form particles of Fe3O4 having a particle size distribution in the above described range; washing the resultant magnetite particles with water, preferably with the assistance of magnetic separation, until the pH of the magnetite dispersion is within the range of about 10-11; depositing a gelatin/polymeric acid coating on the particles by coacervate; and crosslinking. Preferably the coacervation is effected by removing excess water, preferably with the aid of magnetic separation, from the magnetite dispersion that had been washed to pH 10-11 to form a concentrated dispersion of magnetite particles, adding the resulting magnetite dispersion, with stirring, to an aqueous solution, having a temperature of at least about 40° C., of gelatin having an isoelectric point greater than about 8 and a polymeric acid (preferably gum arabic) comprising at least one recurring acid group, preferably selected from the group consisting of carboxylic acid groups and sulfonic acid groups, each of said gelatin and polymeric acid being present in a concentration of from about 1% to about 10% (w/vol) and the ratio of magnetite to the gelatin/polymeric acid mixture on a dry basis being from about 4:1 to about 1:1; and adjusting to coacervation conditions comprising a pH in the range of between about 4 and 5.5 and a concentration of the gelatin/polymeric acid mixture of less than about 2% (wt/vol); and the crosslinking is effected with a known gelatin hardener.

Preferably, each of the gelatin and gum arabic (or other polymeric acid) is present in the aqueous solution of step (5) in a concentration of about 4% (w/vol) and the ratio of magnetite to the gelatin/polymeric acid mixture on a dry basis is preferably about 3:1. Preferably, the coacervation is effected by adjusting the pH with $H_2SO_4$ (or another suitable acid such as acetic acid, or a strong mineral acid, e.g., HCl) to a pH of about 4.0 to 5.5, more preferably a pH of about 4.5; and adding the resulting suspension slowly (over a period of from about 5 to about 30 minutes) with stirring, to a large excess of cold water maintained at a temperature below about 5° C., the resulting suspension being preferably stirred for at least about 30 minutes to stabilize the coacervate coated particles. The crosslinking is preferably effected by rapidly adding to the suspension of stabilized coacervate coated particles a concentrated solution of glutaraldehyde or another gelatin hardener in such amount as to provide the equivalent of at least about 2 gms. of glutaraldehyde per 100 gm. of gelatin on a dry basis, so as to crosslink the gelatin in the coacervate coating on the magnetic particles; stirring, preferably for about 30 minutes, to assure completion of the crosslinking reaction; raising the pH to above 7 with a base such as NaOH; increasing the temperature slowly to about 20-25° C. (ambient); and washing with water to remove unreacted glutaraldehyde.

Preferably the starting ferric and ferrous salts are sulfates. However, other water soluble salts, such as chlorides or other halides, acetates and nitrates can be used.

While the ratio of ferric to ferrous ion in the process of the present invention may be varied within the range of about 1.6 to about 2.4, it is presently preferred that the ratio be approximately 2 so as to provide substantially stoichiometric amounts to satisfy the equation:

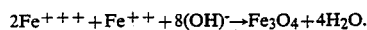

$$2Fe^{+++} + Fe^{++} + 8(OH)^- \rightarrow Fe_3O_4 + 4H_2O.$$

Although sodium dodecyl sulfate is presently preferred for use as the surfactant in the process of the invention, other anionic surfactants and cationic surfactants are also useful and non-ionic surfactants are expected to be useful. A variety of such surfactants can be selected from McCutcheon's Emulsifiers and Detergents, McCutcheon Division, MC Publishing Co., Glen Rock, New Jersey, USA.

Suitable anionic surfactants include Triton 770, an alkylaryl polyether sulfate, sodium salt, sold by Rohm and Haas Co.; Triton X-200, an alkylaryl polyether sulfonate, sodium salt, sold by Rohm and Haas Co.; Triton GR-5M, dioctyl sodium sulfosuccinate, sold by Rohm and Haas Co.; Sterling AM, an ammonium lauryl sulfonate sold by Canada Packers, Inc.; Gafac RM-710, the free acid of a complex organic phosphate ester sold by GAF Corp.; and Witcolate, an alcohol ether sulfate sold by Witco Chem. Corp.

Suitable cationic surfactants include dodecyltrimethylammonium chloride, Ammonyx DMCD-40, a lauryldimethyl amine oxide sold by Onyx Chem. Co.; Ammonyx T, a cetyl dimethyl benzyl ammonium chloride also sold by Onyx Chem Co.; Emcol CC55, a polypropoxy quaternary ammonium acetate sold by Witco Chem Corp.; Triton RW Series, cationic polyalkylene glycols sold by Rohm and Haas Co.; and Emulsifier 3, a quaternary ammonium chloride sold by Tomah Products, Inc.

Suitable non-ionic surfactants include Surfactant 10G, a nonylphenoxypolyglycidol sold by Olin Chem Co.; and various Triton alkylaryloxy polyethoxy ethanols sold by Rohm and Haas Co., such as Triton X-100.

It is preferred to use a substantial excess of hydroxide over the stoichiometric amount in step (2) above, preferably of the order of 10 moles per mole of Fe++. While a ratio of $NaOH/Fe^{++}$ in excess of 10:1 can be used, there does not appear to be an advantage in doing so. While gum arabic is preferably used as the coacervating agent for the gelatin, another polymeric acid comprising recurring acid groups selected from the group consisting of carboxylic acid groups and sulfonic acid groups can be substituted for the gum arabic such as alginic acid, maleic acid, fumaric acid, citraconic acid, itaconic acid, crotonic acid, 3-acrylamidopropanesulfonic acid, 2-acrylamido-2-methylpropanesulfonic acid, 3-acryloyloxypropanesulfonic acid, styrenesulfonic acid, etc., typical comonomers being alkyl acrylates and alkyl methacrylates such as methyl methacrylate, ethyl acrylate, and vinyl monomers such as ethylene, e.g., partially hydrolyzed poly(ethylene-co-maleic anhydride), methyl vinyl ether, styrene, vinyl acetate, e.g., partially hydrolyzed poly(vinyl acetate-co-maleic anhydride), amides such as acrylamide, methacrylamide and N-isopropylacrylamide. The molecular weights of the polymers can range from about 5,000 to 300,000.

When gum arabic is used, the preferred weight ratio of gelatin to gum arabic is 1:1, although this ratio can conveniently be within the range of 2:1 to 1:2. When other polymeric acids, preferably polycarboxylic or polysulfonic acids, are substituted for gum arabic, the ratios can be adjusted accordingly.

Similarly, while the presently preferred ratio of magnetite to coacervate on a dry basis is about 3:1, this ratio can conveniently be selected within the range of about 4:1 to 1:1.

Preferably, the ratio of suspension to cold water in the quenching step described above is about 1 liter of suspension to about 8-10 liters of cold water.

While glutaraldehyde is the presently preferred crosslinking agent for use in the process of this invention, other gelatin hardeners known to those skilled in the photographic arts can be substituted, with suitable adjustments as may be required to maintain equivalent stoichiometry.

Typical useful gelatin hardeners include formaldehyde and dialdehydes such as succinaldehyde and glutaraldehyde as described in U.S. Pat. No. 3,232,764; active esters such as described in U.S. Pat. No. 3,542,558; active halogen compounds such as described in U.S. Pat. Nos. 3,106,468, 3,305,376 and 3,957,882; s-triazines such as described in U.S. Pat. No. 3,325.287; aziridines such as described in U.S. Pat. No. 3,575,705; active olefins such as described in U.S. Pat. Nos. 3,490,911 and 3,640,720; vinylsulfones such as bis(vinylsulfonylmethyl) ether and bis(vinylsulfonyl)-methane as described in U.S. Pat. No. 3,841,872 and U.S. Pat. No. 3,539,644; halogen-substituted aldehyde acids such as mucochloric and mucobromic acids; and polymeric hardeners such as dialdehyde starches poly(acrolein-co-methacrylic acid); poly(styrene-co-2-chloroethylsulfonylmethylstyrene) and poly(styrene-co-vinylsulfonylmethylstyrene).

The coacervate coated superparamagnetic particles of the present invention have a mean diameter in the range of from about 70 Å to about 450 Å, preferably from about 100 Å to about 400 Å, more preferably from about 150 Å to about 350 Å and comprise magnetite particles having a mean diameter in the range of from about 50 Å to about 350 Å, preferably about 100 Å to about 300 Å, more preferably about 150 Å to about 250 Å, that are coated with a coating that is from about 20 Å to about 100 Å thick, preferably about 30 Å to about 50 Å thick, which coating comprises a crosslinked coacervate of gelatin with gum arabic or another polymeric acid, preferably one containing repeating units of a carboxylic acid or a sulfonic acid; the magnetite particles, before being coated, having a magnetization of greater than about 30 emu/gm, preferably greater than about 40 emu/gm, more preferably greater than about 50 emu/gm and a coercive force of less than about 30 Oe, preferably less than about 25 Oe, more preferably than about 20 Oe. The coated particles have a magnetization greater than about 30 emu/gm preferably greater than about 40 emu/gm and a coercive force less than about 30 Oe, preferably less than about 25 Oe, more preferably less than about 20 Oe. The magnetization and coercive force values of the paramagnetic particles as set forth herein are values obtained by using a VSM meter while applying a magnetic field of 2500 Oe to the dry particles.

As previously indicated, the coated superparamagnetic particles of the invention can be used in known techniques for separation of biological materials, as described, for example, in U.S. Pat. No. 4,672,040 and discussed in the Description Relative to the Prior Art hereinabove, as well as in drug delivery systems, for diagnostic imaging and in other applications wherein it is advantageous to use fine superparamagnetic particles having a narrow particle size distribution, particularly where biocompatability is important.

The following examples are presented to illustrate the practice of &he present invention:

EXAMPLE 1

The pH of 100 ml of an equimolar mixture of ferrous and ferric sulfate was adjusted to 1.0 with 25% sulfuric acid. To this was added 10 ml. of a 4% gelatin solution acid processed (pI-9) whose pH had been adjusted to 0.8 with sulfuric acid solution. The temperature was raised to 50° C. and 25% sodium hydroxide solution was added over a period of five minutes to give a final pH of 12.5. During this time, the solution was stirred in the presence of air. The black suspension was separated magnetically and washed with distilled water. The washed magnetite precipitate was then mixed with 100 ml. of a solution containing 4% w/vol of each of gelatin and gum arabic. The gelatin was the same type as used in the magnetite preparation step described above. The mixture of magnetite and gelatin-gum arabic was agitated at 40° C. and the pH was lowered to 4.5 with 25% HCl. This mixture was then poured slowly into 500 ml. of water that was agitated rapidly at 4.5° C. After 30 minutes, 20 ml. of 50% glutaraldehyde was added, and the gelatin coating was considered to be fully crosslinked and the encapsulated magnetite was washed several times by distilled water, using magnetic separation.

Electron microscope examination showed the particles to be 100–150 Å in diameter, with a very minor 40–50 Å fraction. Elemental analysis was used to determine the gelatin-gum arabic content, and estimates of shell thickness of 31 Å were calculated (assuming the magnetite particle diameter to be 100 Å). Magnetic evaluation is shown in FIG. 1.

It can be readily seen from the magnetization curve that no hysteresis exists.

Magnetic separation was demonstrated by inserting a plug of steel wool (fine grade) approximately 3 cm long and 1.5 cm ID into the stem of a small plastic powder funnel. The stem was placed between the poles of a small horseshoe magnet (800 gauss), and the encapsulated magnetite solution poured into the funnel. Clear liquid drained out. Removing the magnet and pouring the clear liquid into the funnel caused the particles to be removed from the steel wool. The recovery was excellent, which is further proof that the particles are superparamagnetic.

EXAMPLE 2

Example 1 was repeated, but 0.5% of dodecyltrimethylammonium chloride was used as a surfactant/dispersing agent instead of gelatin in the preparation of the magnetite. The encapsulation step involving gelatin and gum arabic was carried out exactly as described in Example 1, and the results were comparable.

EXAMPLE 3

This example illustrates the hydrophobizing of the gelatin-gum arabic shell so that the encapsulated $Fe_3O_4$ particles have an affinity for non-water-miscible organic solvents such as toluene or ethylbenzene, thus making them useful in non-aqueous systems such as ferro fluids. (See, for example, U.S. Pat. No. 3,531,413.)

One gram of the wet coagulum of Example 1 was mixed with 15 ml. of water and 1 ml. of Quilon M (DuPont), and the mixture was shaken for five days. Another sample, which consisted of the unencapsulated magnetite preparation was also treated in this manner. The samples were then decanted and rinsed several times with water, decanting magnetically between rinses. They were then rinsed three times with methanol, decanting magnetically between rinses, after which they were mixed with ethylbenzene. Comparison with untreated samples of encapsulated magnetite and unencapsulated magnetite particles that were washed in the same manner showed that only the Quilon treated encapsulated magnetite had much slower sedimentation rates. This indicates that the Quilon had reacted with the surface of these magnetic samples and had attached so that the surfaces were now hydrophobic.

Quilon is a chrome complex sold by the DuPont Corporation in which myristic acid is coordinated with trivalent chromium. The commercial solution (in isopropanol) contains 5.7% (by weight) chromium and 11.7% fatty acid. The anion is chloride (7.8%). Quilon is generally used to impart water repellancy to paper and fabric.

Other hydrophobizing agents such as alkyl titanites, silanes and borates could also be used.

EXAMPLE 4

A suspension of magnetite particles that had been encapsulated by gelatin gum arabic coacervate as described in Example 1 was prepared mixing 2.34 grams of a concentrated dispersion (13% wt/vol, dry basis) of the particles with 25 ml. of distilled water. This was stirred for 3 minutes in a high speed (Virtis) mixer at 23,000 rpm for 3 minutes. Twenty-five ml. of a 2% solution of benzoquinone was added and the pH raised to 11.1 with sodium hydroxide. This mixture was shaken for 18 hours, after which it was magnetically separated and washed three times with distilled water, followed by two washes with methanol. It was dried at 75° C. Combustion analysis showed that the gelatin-gum arabic shell had reacted with the benzoquinone so that 14% of the modified shell was benzoquinone.

EXAMPLE 5

A suspension of encapsulated magnetite was prepared as described in Example 1 and mixed with a solution of glutaraldehyde (1%). This was shaken for 2½ days after which it was magnetically separated and washed with water (3 cycles). The washed particles were mixed with a 2% gelatin (isoelectric point 8.3) solution and stirred at 40° C. for 18 hours. It was then magnetically separated and washed 3 times with 35° distilled water. This was followed by two methanol washes. Analysis showed that the gelatin-gum arabic shell had doubled in weight due to the coupling of gelatin in the solution with the glutaraldehyde activated particle surface.

EXAMPLE 6

A suspension of encapsulated magnetite was prepared as described in Example 1 and mixed with a solution containing 2% gum arabic and 5% butanediol bis(glycidyl) ether. This was shaken for 6 days after which it was separated magnetically and washed with water. This was followed by a methanol wash. Analysis showed that the particles had reacted with a substantial amount of gum arabic through the epoxide coupling to the encapsulated magnetite particle. The shell had undergone a 50% increase in weight.

EXAMPLE 7

Two hundred ml. of a solution that is 1 molar in both ferrous and ferric sulfate were prepared and the resultant mixture made 1% in sodium dodecyl sulfate. The solution was purged of dissolved oxygen by passing nitrogen through for 30 minutes at 25° C. To the rapidly stirred mixture, 40 gms. of sodium hydroxide in 80 ml. water was rapidly added and the stirring continued under nitrogen for one hour. After this period of time, the reaction mixture was poured into an excess of water. The magnetite was separated magnetically and washed with distilled water until the pH of the wash water was below 11. The reaction mixture was identified as $Fe_3O_4$ by means of X-Ray diffraction. The magnetization and coercive force values were: 56.9 emu/g and 15.4 Oe respectively. A coercive force below 30 Oe is indicative of a superparamagnetic material.

The wet magnetite paste was dispersed in 200 ml. of a gelatin gum arabic solution in which each of the gelatin and gum arabic was present in a concentration of 4% wt/vol. The gelatin had an isoelectric point of approximately 8.5. The mixture was agitated at 40° C. and the pH lowered to 4.5 with 25% sulfuric acid. This mixture was then poured slowly into 2 liters of water that was agitated rapidly at 4° C. After 30 minutes, 4 ml. of 50% glutaraldehyde was added and the suspension of coacervated magnetite was stirred for a additional 30 minutes at 4° C. The pH was then raised to 10 with sodium hydroxide and the solution allowed to come to room temperature. At this point, the coacervate shells were fully crosslinked, and the encapsulated magnetite was washed several times with distilled water at room temperature using magnetic separation between the washes. Electron microscopic examination showed the particles to be 100-150 Å in diameter with a very minor 40-50 Å fraction. Elemental analysis was used to determine the gelatin-gum arabic content and estimates of shell thickness of 31 Å were calculated assuming the magnetite particle diameter to be 100 Å.

EXAMPLE 8

U.S. Pat. No. 4,582,622 describes the encapsulation of magnetic particles by a process which involves the deposition of a mixture consisting of gelatin, gum arabic, and sodium polymetaphos-phate. The procedure set forth in Example 1 of the patent was followed with the substitution of sodium dodecyl sulfate for the surfactants there used (alkylsulfomaleate, sodium oleate, and Demol Ep).

Three variations with regard to the quantity of magnetite were made: (1) the concentration used in Example 1 of the patent, which is very low, (2) a 5 fold and (3) a 10 fold increase therefrom.

All particles prepared showed very coarse aggregation with dimensions ranging from 1 to 10 microns. Separation using the steel wool funnel as described in Example 1 (of this application) was unsuccessful in that the particles could not be washed off the steel wool after the magnetic field had been removed.

The invention has been described in detail with particular reference to preferred embodiments thereof, but it will be understood that variations and modifications can be effected within the spirit and scope of the invention.

What is claimed is:

1. Encapsulated superparamagnetic particles having a narrow particle size distribution, the mean diameter of the particles being within the range of from about 70 Å to about 450 Å, said particles comprising particles of magnetite having a narrow particle size distribution, the mean diameter of the magnetite particles being between about 50 Å and about 350 Å, said magnetite particles having a magnetization of greater than about 30 emu/gm and a coercive force of less than about 30 Oe, said magnetite particles being encapsulated with a coating of a crosslinked coacervate of gelatin and a polymeric acid and wherein the weight ratio of magnetite to coacervate in said encapsulated particles on a dry basis is from 4:1 to 1:1.

2. The superparamagnetic particles of claim 1 wherein said polymeric acid comprises recurring acid groups selected from the group consisting of carboxylic acid groups and sulfonic acid groups.

3. The encapsulated particles of claim 1 wherein at least 80% of the magnetite particles have diameters in the range of between about 100 Å and about 300 Å.

4. The encapsulated particles of claim 1 wherein the magnetite particles have a magnetization greater than 40 emu/gm.

5. The encapsulated particles of claim 1 wherein the magnetite particles have a coercive force less than about 25 Oe.

6. The encapsulated particles of claim 1 which have mean diameters within the range of from about 100 Å to about 400 Å.

7. The encapsulated particles of claim 1 wherein at least 80% of the particles have mean diameters within the range of from about 150 Å to about 350 Å.

8. The encapsulated particles of claim 1 wherein the magnetite particles have a magnetization greater than about 50 emu/gm and a coercive force less than about 25 Oe.

9. The encapsulated particles of claim 1 which have a magnetization greater than about 30 emu/gm and a coercive force less than about 25 Oe.

10. The encapsulated particles of claim 1 wherein the coacervate coating has an average thickness of between about 30 Å and about 100 Å.

11. A method for preparing the stable, coated, superparamagnetic magnetite particles of claim 1 having a narrow particle size distribution which consists essentially of forming an equeous solution of ferric and ferrous salts by adding a mixture of ferric and ferrous salts to water in amounts that provide a molar ratio of ferric to ferrous ion in the range of from about 1.6 to 2.4 and in concentrations in the range of from about 0.1 to 1 molar; adding to the solution concentrated hydroxide in an amount in excess of 8 moles of $OH^-$ per mole of ferrous ion present in the solution to form a dispersion of fine particles of magnetite; washing the resultant magnetite particles with water until the pH of the magnetite dispersion is within the range of about 10-11; depositing a coating of gelatin and a polymeric acid on the particles by removing excess water from the magnetite dispersion that had been washed to said pH of 10-11; to form a concentrated dispersion of magnetite particles, then coating the thus produced particles by adding the resulting magnetite dispersion to an aqueous solution, having a temperature of at least about 40° C., said aqueous solution consisting essentially of gelatin having an isoelectric point greater than about 8 and a polymeric acid comprising at least one recurring acid group; and adjusting to coacervation conditions comprising a pH in the range of between about 4.0 and 5.5 and a concentration of the gelatin/polymeric acid mixture of less than about 2% (wt/vol); and then crosslinking to form and produce.

12. The method of claim 11 wherein the molar ratio of ferric to ferrous ions is about 2.

13. The method of claim 11 wherein the ferric and ferrous salts are sulfates.

14. The method of claim 11 wherein the concentration of the salts is about 0.1 molar.

15. The method of claim 11 which further comprises adding sufficient acid to the aqueous mixture of ferric and ferrous salts to adjust the pH to less than about 1.5.

16. The method of claim 15 wherein the acid is sulfuric acid.

17. The method of claim 11 which further comprises adding from about 0.1 to about 5% (wt/vol) of a surfactant to the salt solution.

18. The method of claim 17 wherein the surfactant is sodium dodecyl sulfate.

19. The method of claim 11 which further comprises purging the solution of oxygen by bubbling therethrough an inert gas for a period of at least about 10 minutes.

20. The method of claim 19 wherein said bubbling is continued for at least about 30 minutes.

21. The method of claim 11 wherein the concentrated hydroxide comprises NaOH in an amount equivalent to about 10 moles per mole of ferrous ion present in the salt solution.

22. The method of claim 11 wherein each of said gelatin and polymeric acid are present in a concentration of from about 1% to about 10% (w/vol) and the ratio of magnetite to the gelatin/polymeric acid mixture on a dry basis being from about 4:1 to about 1:1.

23. The method of claim 11 wherein said recurring acid group is selected from the group consisting of carboxylic acid groups and sulfonic acid groups.

24. The method of claim 11 wherein the coacervate is crosslinked with a suitable crosslinking agent for gelatin.

25. The method of claim 11 wherein the gelatin has an isoelectric point of at least about 8.5.

26. The method of claim 11 wherein the polymeric acid is gum arabic.

27. The method of claim 11 wherein said adjusting to coacervating conditions comprises adding to the dispersion of magnetite containing gelatin and polymeric acid sufficient concentrated acid solution to provide said pH within the range of from about 4.0 to 5.5.

28. The method of claim 27 which further comprises adding the resulting suspension slowly, with stirring, to a large excess of cold water maintained at a temperature below about 5° C. and stirring to stabilize the coacervate coated particles.

29. The method of claim 24 wherein said crosslinking agent is a gelatin hardener.

30. The method of claim 29 wherein the gelatin hardener is glutaraldehyde.

31. The method of claim 30 wherein said glutaraldehyde is added in a concentrated solution containing sufficient glutaraldehyde to provide at least about 2 gms. of glutaraldehyde per 100 gm. of gelatin on a dry basis.

32. The method of claim 24 wherein said crosslinking step includes stirring for a sufficient time to assure completion of the crosslinking reaction, raising the pH to above 7, increasing the temperature to about 20–25° C., and washing with water to remove unreacted crosslinking agent.

33. The method of claim 32 wherein said pH is raised to at least about 10.

* * * * *